US00PP34358P2

(12) United States Plant Patent
Mathey

(10) Patent No.: US PP34,358 P2
(45) Date of Patent: Jun. 21, 2022

(54) ***WEIGELA* PLANT NAMED 'SMNWFGC'**

(50) Latin Name: *Weigela florida*
Varietal Denomination: SMNWFGC

(71) Applicant: Megan M. Mathey, Holland, MI (US)

(72) Inventor: Megan M. Mathey, Holland, MI (US)

(73) Assignee: SPRING MEADOW NURSERY Inc., Grand Haven, MI (US)

( * ) Notice: Subject to any disclaimer, the term of this patent is extended or adjusted under 35 U.S.C. 154(b) by 0 days.

(21) Appl. No.: 17/492,628

(22) Filed: Oct. 3, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Weigela* plant named 'SMNWFGC', characterized by its upright to outwardly spreading and uniformly mounding plant habit; freely branching habit; dense and bushy appearance; leaves that are dark purple to dark reddish brown in color; freely flowering habit; light yellow green-colored flower buds and white-colored flowers; and good garden performance.

2 Drawing Sheets

Figure 1:
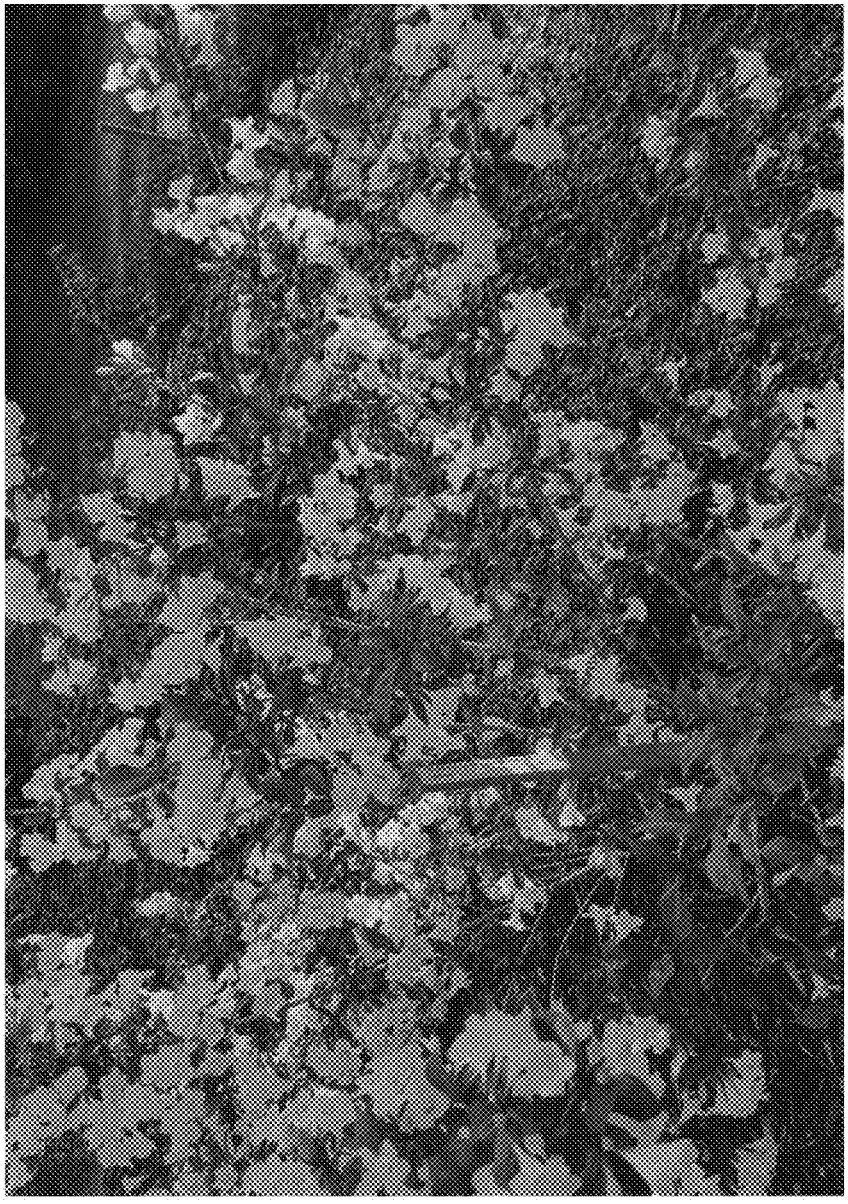

Botanical designation: *Weigela florida.*
Cultivar denomination: 'SMNWFGC'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Weigela* plant, botanically known as *Weigela florida* and hereinafter referred to by the name 'SMNWFGC'.

The new *Weigela* plant is a product of a planned breeding program conducted by the Inventor in Grand Haven, Mich. The objective of the breeding program was to develop new compact and freely flowering *Weigela* plants with dark-colored leaves and white-colored flowers.

The new *Weigela* plant originated from an open-pollination in 2016 in Grand Haven, Mich. of *Weigela florida* 'Granitini', not patented, as the female, or seed, parent with an unknown selection of *Weigela florida* as the male, or pollen, parent. The new *Weigela* plant was discovered and selected by the Inventor in 2018 as a single flowering plant within the progeny of the stated open-pollination in a controlled environment in Grand Haven, Mich.

Asexual reproduction of the new *Weigela* plant by softwood stein cuttings since 2018 in Grand Haven, Mich. has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNWFGC'. These characteristics in combination distinguish 'SMNWFGC' as a new and distinct *Weigela* plant:

1. Upright to outwardly spreading and uniformly mounding plant habit.
2. Freely branching habit; dense and bushy appearance.
3. Leaves that are dark purple to dark reddish brown in color.
4. Freely flowering habit.
5. Light yellow green-colored flower buds and white-colored flowers.
6. Good garden performance.

In side-by-side comparisons conducted in Grand Haven, Mich., plants of the new *Weigela* differ primarily from plants of the female parent, 'Granitini', in the following characteristics:

1. Plants of the new *Weigela* have darker-colored leaves than plants of 'Granitini'.
2. Plants of the new *Weigela* have smaller flowers than plants of 'Granitini'.
3. Plants of the new *Weigela* have white-colored flowers whereas plants of 'Granitini' have white-colored flowers that are tinged with pink.

Plants of the new *Weigela* can also be compared to plants of the *Weigela florida* 'Velda', disclosed in U.S. Plant Pat. No. 26,842. In side-by-side comparisons plants of the new *Weigela* differ primarily from plants of 'Velda' in the following characteristics:

1. Plants of the new *Weigela* have darker-colored leaves than plants of 'Velda'.
2. Plants of the new *Weigela* are more freely flowering than plants of 'Velda'.
3. Flower buds of plants of the new *Weigela* are brighter yellow green in color than flower buds of plants of 'Velda'.
4. Flowers of plants of the new *Weigela* are white in color whereas flowers of plants of 'Velda' are white in color with a yellow orange-colored streak in the throat.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet (FIG. 1) is a side perspective view of a typical plant of 'SMNWFGC' grown in an outdoor nursery.

Figure 2:
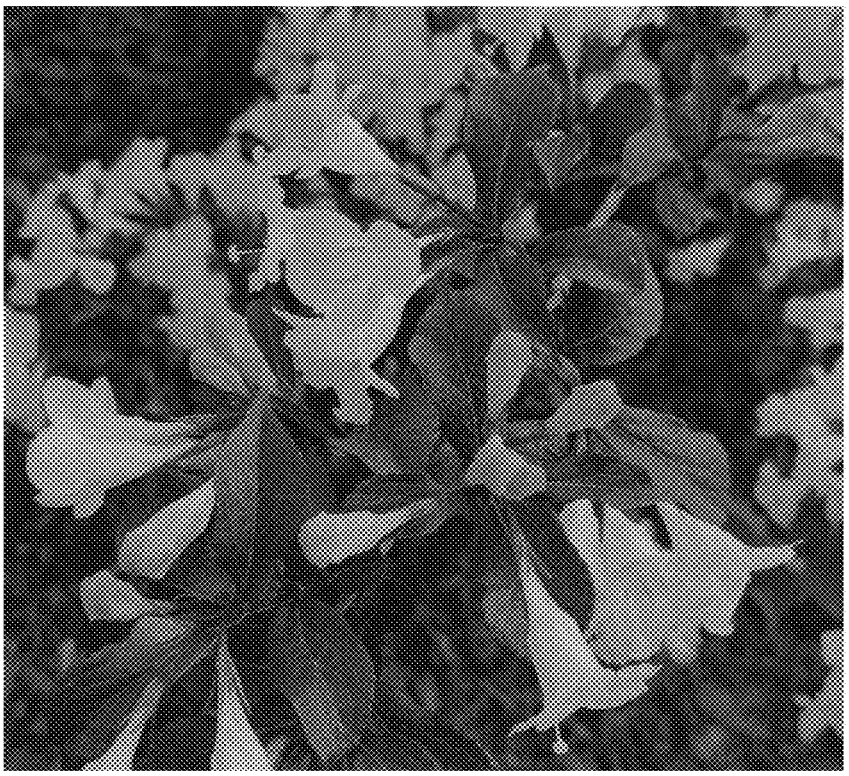

The photograph on the second sheet (FIG. 2) is a close-up view of a typical flowering plant of 'SMNWFGC'.

DETAILED BOTANICAL DESCRIPTION

Plants used for the aforementioned photographs and the following description were grown during the spring and summer in ground beds in an outdoor nursery and in three-gallon containers in a polypropylene- covered greenhouse in Grand Haven, Mich. and under cultural practices typical of commercial *Weigela* production. During the production of the plants, day temperatures ranged from 18° C. to 27° C. and night temperatures ranged from 5° C. to 10° C. Plants of the new *Weigela* were two years old when the photographs and description were taken. In the following description, color references are made to The Royal Horticultural Society Colour Chart, 2015 Edition, except where general terms of ordinary dictionary significance are used.

Botanical classification: *Weigela florida* 'SMNWFGC'.

Parentage:

*Female, or seed, parent.*—*Weigela florida* 'Granitini ', not patented.

*Male, or pollen, parent.*—Unknown selection of *Weigela florida*, not patented.

Propagation:

*Type.*—By softwood stein cuttings.

*Time to initiate roots, summer.*—About 15 days at temperatures about 18° C. to 27° C.

*Time to produce a rooted young plant, summer.*—About two months at temperatures about 18° C. to 27° C.

*Root description.*—Fine; fibrous; typically white in color, actual color of the roots is dependent on substrate composition, water quality, fertilizer, substrate temperature and physiological age of roots.

*Rooting habit.*—Freely branching; dense.

Plant description:

*Plant and growth habit.*—Perennial shrub; upright to outwardly spreading and uniformly mounding plant habit; vigorous growth habit and rapid growth rate.

*Branching habit.*—Freely branching habit with about 15 to 20 lateral branches developing per plant; pinching enhances lateral branch development; dense and bushy plant form.

*Plant height.*—About 45 cm.

*Plant diameter.*—About 55 cm.

Lateral branch description:

*Length.*—About 40 cm.

*Diameter.*—About 2 mm to 6 mm.

*Internode length.*—About 4 cm.

*Texture.*—When developing, slightly pubescent along longitudinal ridges; with development becoming glabrous.

*Strength.*—Strong, somewhat flexible.

*Aspect.*—About 15° to 45° from vertical.

*Color, developing.*—Close to between 166B and 200A.

*Color, developed.*—Close to 199C.

Leaf description:

*Arrangement.*—Opposite; simple.

*Length.*—About 8 cm.

*Width.*—About 3.75 cm.

*Shape.*—Elliptical to oblanceolate.

*Apex.*—Acuminate.

*Base.*—Oblique.

*Margin.*—Serrulate.

*Texture, upper surface.*—Smooth, glabrous; coriaceous.

*Texture, lower surface.*—Pubescence along midvein; prominent venation; coriaceous.

*Venation pattern.*—Pinnate.

*Color.*—Developing leaves, upper surface: Close to 147A; towards the margins, tinged with close to between N186A and 200A. Developing leaves, lower surface: Close to 147B; towards the margins, tinged with close to between N186A and 200A. Fully expanded leaves, upper surface: Close to between N186A and 200A; proximally, close to 147A; venation, close to 147A tinged with close to N186A. Fully expanded leaves, lower surface: Close to 148A tinged with close to N186A; venation, close to 147C.

*Petioles.*—Length: About 3 mm. Diameter: About 3 mm. Texture, upper and lower surfaces: Slightly pubescent. Color, upper and lower surfaces: Close to between N186A and 200A.

Flower description:

*Flower arrangement and habit.*—Salverform flowers arranged in terminal clusters each with about four to six flowers; about 50 flowers develop per lateral stem during the flowering season; flowers face upright to slightly outwardly.

*Fragrance.*—None detected.

*Natural flowering season.*—Plants of the new *Weigela* flower during the late spring and early summer in Grand Haven, Mich.; flowers not persistent.

*Flower buds.*—Length: About 2 cm. Diameter: About 7 mm. Shape: Obovate to spatulate. Color: Close to between 145B to 145C.

*Flower diameter.*—About 2.5 cm.

*Flower length (height).*—About 3 cm.

*Flower throat diameter.*—About 1 cm

*Flower tube length.*—About 1.5 cm.

*Flower tube diameter, proximally*.—About 3 mm.

*Corolla*.—Arrangement: Salverform; five petals fused into a tube with separate petal lobes. Petal lobe length: About 1 cm. Petal lobe width: About 1 cm. Petal lobe shape: Rounded to orbicular. Petal lobe apex: Obtuse. Petal lobe margin: Entire; slightly undulate. Petal texture, upper and lower surfaces: Smooth, glabrous; silky. Throat and tube texture: Smooth, glabrous. Color: Developing and fully developed, upper surface: Close to NN155B slightly tinged with close to 150D; venation, similar to lamina color. Developing and fully developed, lower surface: Close to NN155B slightly tinged with close to 150D; venation, similar to lamina color. Throat: Close to NN155B; venation, close to NN155B. Tube: Close to NN155B; towards the base, close to 76D; venation, close to NN155B.

*Sepals*.—Quantity per flower: Five in a single whorl, fused; campanulate calyx. Length: About 1 cm. Width: About 2 mm. Shape: Narrowly triangular, elongated. Apex: Acuminate. Base: Obtuse. Margin: Entire. Sepal texture, upper and lower surfaces: Smooth; glabrous; coriaceous. Color, upper and lower surfaces: Close to N187A; towards the base, close to 144B.

*Peduncles*.—Length: About 1.5 cm. Diameter: About 2 mm. Strength: Strong. Aspect: Upright to outwardly. Texture: Smooth, glabrous. Color: Close to N187A.

*Reproductive organs*.—Stamens: Quantity and arrangement: Five per flower. Filament length: About 1 cm. Filament color: Close to NN155B. Anther shape: Narrowly oblong. Anther size: About 5 mm. Anther color: Close to 161A. Pollen amount: None observed. Pistils: Quantity: One per flower. Pistil length: About 3.5 cm. Style length: About 3 cm. Style color: Close to NN155B; towards the base, close to 76D. Stigma shape: Flattened globular. Stigma color: Close to NN155B. Seeds and fruits: To date, seed and fruit development has not been observed on plants of the new *Weigela*.

Garden performance: Plants of the new *Weigela* have exhibited good garden performance.

Pathogen & pest resistance: To date, plants of the new *Weigela* have not been observed to be resistant to pathogens and pests common to *Weigela* plants.

It is claimed:

1. A new and distinct *Weigela* plant named 'SMNWFGC' as illustrated and described.

* * * * *